US010925597B2

(12) United States Patent
Deane et al.

(10) Patent No.: US 10,925,597 B2
(45) Date of Patent: Feb. 23, 2021

(54) MEDICAL SECURING DEVICE FOR SECURING AN OBJECT WITH A SECURING MEMBER

(71) Applicant: Medtentia International Ltd Oy, Espoo (FI)

(72) Inventors: Stuart Deane, Collooney (IE); Jake O'Regan, Collooney (IE); Ger O'Carroll, Collooney (IE); Mark Pugh, Collooney (IE); Hans-Reinhard Zerkowski, Kreuzlingen TG (CH); Olli Keränen, Bjärred (SE)

(73) Assignee: Medtentia International Ltd Oy, Espoo (FI)

( * ) Notice: Subject to any disclaimer, the term of this patent is extended or adjusted under 35 U.S.C. 154(b) by 326 days.

(21) Appl. No.: 15/393,386

(22) Filed: Dec. 29, 2016

(65) Prior Publication Data
US 2018/0185020 A1     Jul. 5, 2018

(51) Int. Cl.
*A61B 17/04*       (2006.01)
*A61F 2/24*        (2006.01)
(Continued)

(52) U.S. Cl.
CPC ...... *A61B 17/0469* (2013.01); *A61B 17/0467* (2013.01); *A61B 2017/00367* (2013.01); (Continued)

(58) Field of Classification Search
CPC ............ A61B 17/0469; A61B 17/0467; A61B 17/0482; A61B 17/0483; A61B 17/062; A61B 17/0625; A61B 2017/047; A61B 2017/0472; A61B 2017/0475; A61B 2017/0477; A61B 17/0485; (Continued)

(56) References Cited

U.S. PATENT DOCUMENTS

2004/0181238 A1   9/2004   Zarbatany
2009/0018554 A1*  1/2009   Thorne ............... A61B 17/0485
                                                  606/145
(Continued)

FOREIGN PATENT DOCUMENTS

| EP | 1853199 | 8/2006 |
|----|---------|--------|
| EP | 2952138 A1 | 12/2015 |
| WO | 20160196579 A1 | 12/2016 |

OTHER PUBLICATIONS

Search report of EP16207290.4 issued by European Patent Office dated Jun. 7, 2017.

*Primary Examiner* — Katherine H Schwiker
(74) *Attorney, Agent, or Firm* — Berggren LLP

(57) ABSTRACT

A medical securing device for securing an object with a securing member into a tissue comprises an elongated sheath comprising proximal and distal ends, and a securing member introduction device having proximal and distal ends, said distal end being configured to extend from the sheath. The medical securing device comprises also a guiding trail. At least one point of the securing member introduction device is configured to travel along said first guiding trail and thereby control a defined movement of the distal end of said securing member introduction device when extending from the sheath and so to introduce the securing member to the object and to secure said object to the tissue with the securing member.

10 Claims, 8 Drawing Sheets

(51) Int. Cl.
*A61B 17/00* (2006.01)
*A61B 17/06* (2006.01)

(52) U.S. Cl.
CPC ............... *A61B 2017/00535* (2013.01); *A61B 2017/00783* (2013.01); *A61B 2017/00876* (2013.01); *A61B 2017/0472* (2013.01); *A61B 2017/06042* (2013.01); *A61F 2/2445* (2013.01); *A61F 2220/0008* (2013.01)

(58) Field of Classification Search
CPC ........ A61B 17/0491; A61B 2017/0409; A61B 2017/0411; A61B 2017/0416; A61B 2017/0479; A61B 2017/06052; A61B 2017/00663; A61B 2017/06042; A61F 2/2442; A61F 2/2445; A61F 2/2448; A61F 2/2466; A61F 2/2457; A61F 2220/0008
USPC .................................................. 606/144–147
See application file for complete search history.

(56) References Cited

U.S. PATENT DOCUMENTS

| | | | |
|---|---|---|---|
| 2010/0016870 A1* | 1/2010 | Campbell | A61B 17/04 606/144 |
| 2010/0113873 A1* | 5/2010 | Suzuki | A61B 1/00096 600/106 |
| 2010/0198235 A1* | 8/2010 | Pierce | A61B 17/0469 606/148 |
| 2011/0245850 A1* | 10/2011 | van der Burg | A61B 90/39 606/145 |
| 2011/0295279 A1* | 12/2011 | Stone | A61B 17/0469 606/145 |
| 2012/0283750 A1 | 11/2012 | Saliman | |
| 2014/0058417 A1* | 2/2014 | Levy | A61F 2/0063 606/151 |
| 2014/0163323 A1* | 6/2014 | Mohajer-Shojaee | A61B 17/3498 600/204 |
| 2015/0018850 A1* | 1/2015 | Bagaoisan | A61B 17/0469 606/144 |
| 2015/0283750 A1 | 10/2015 | Kenny et al. | |

* cited by examiner

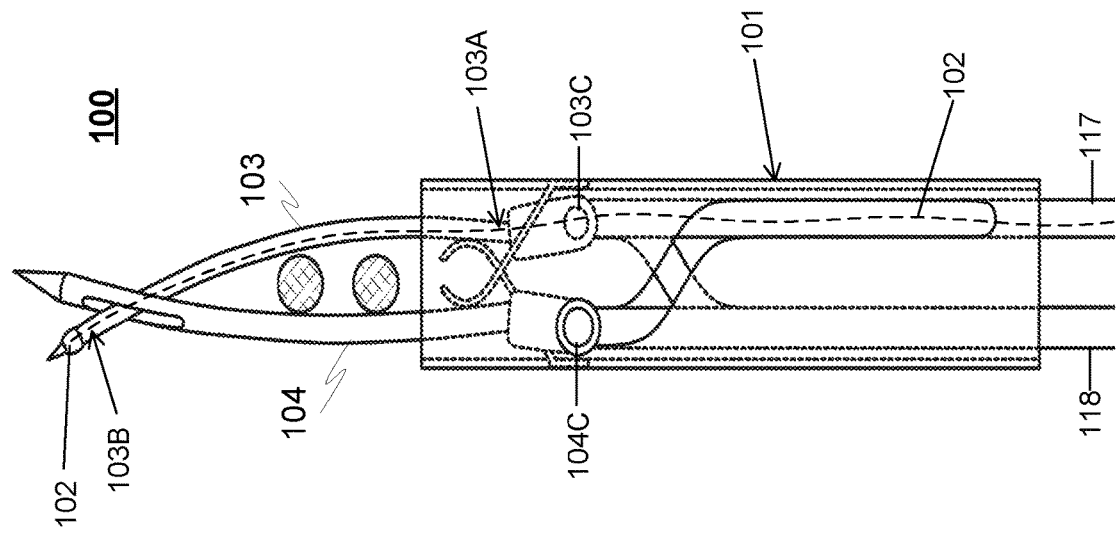
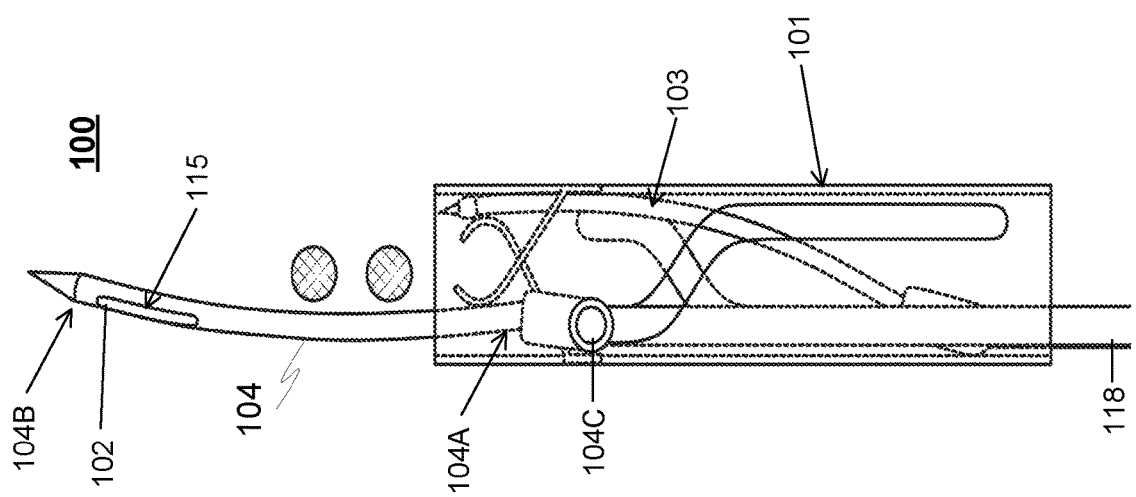
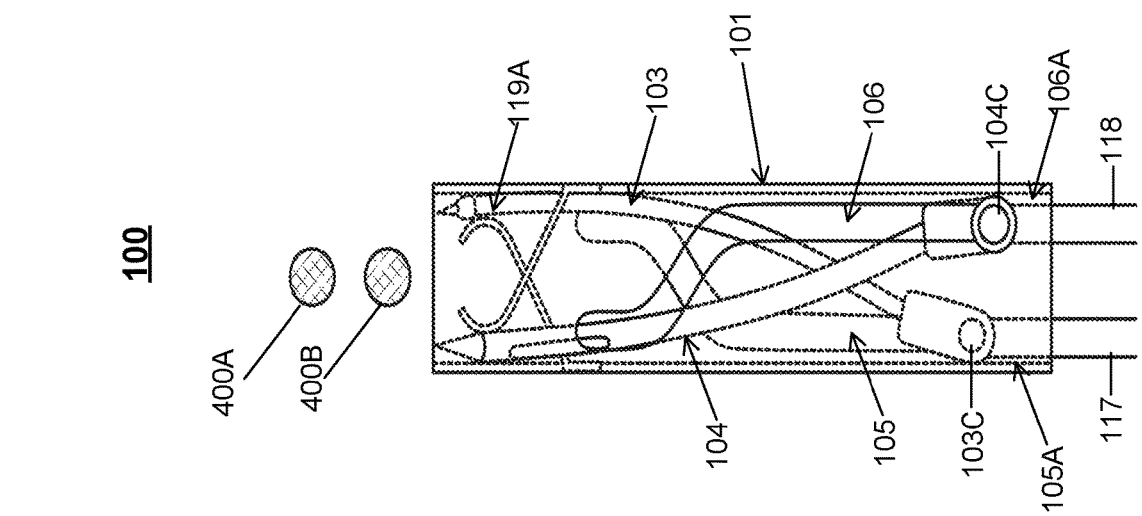

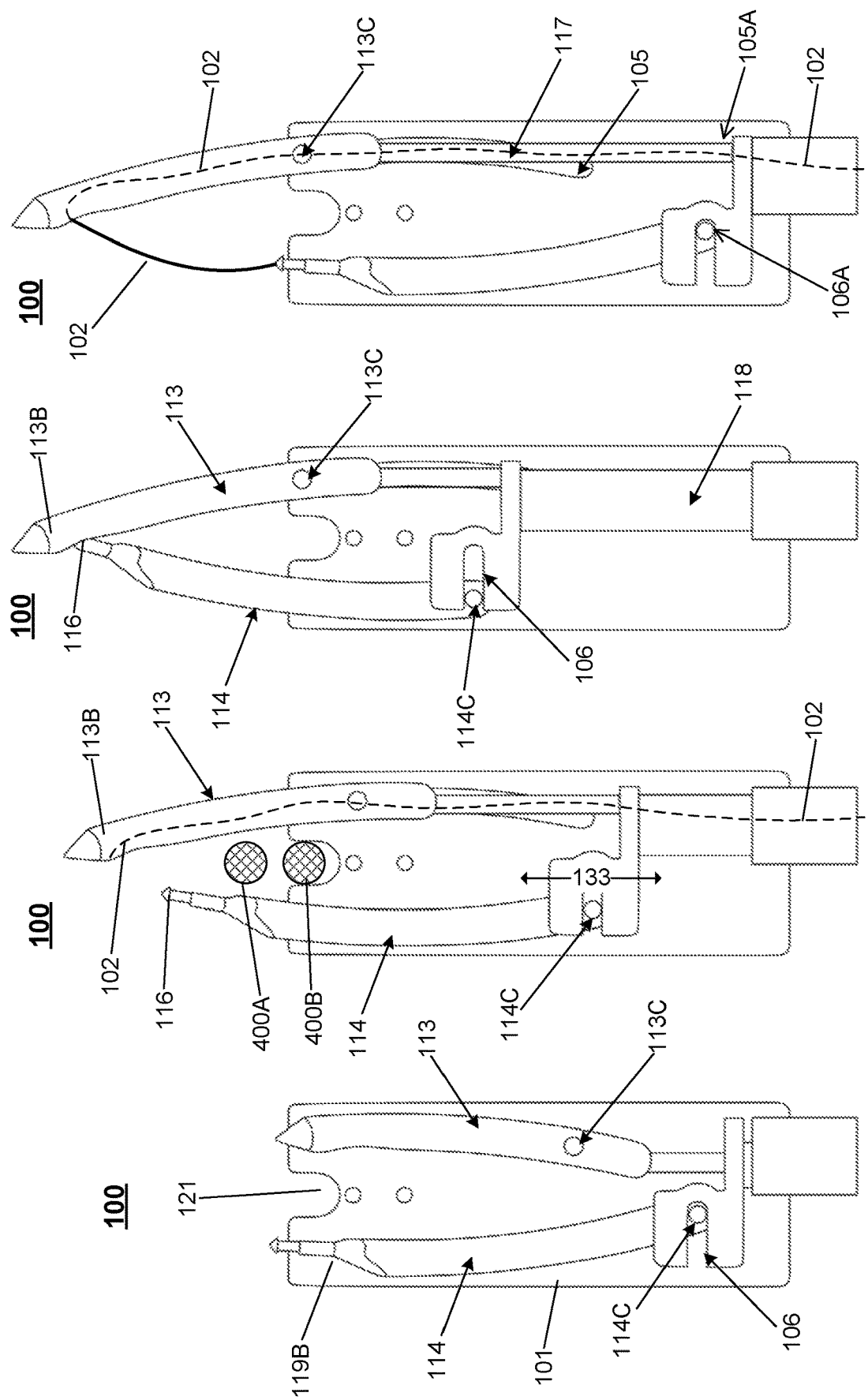

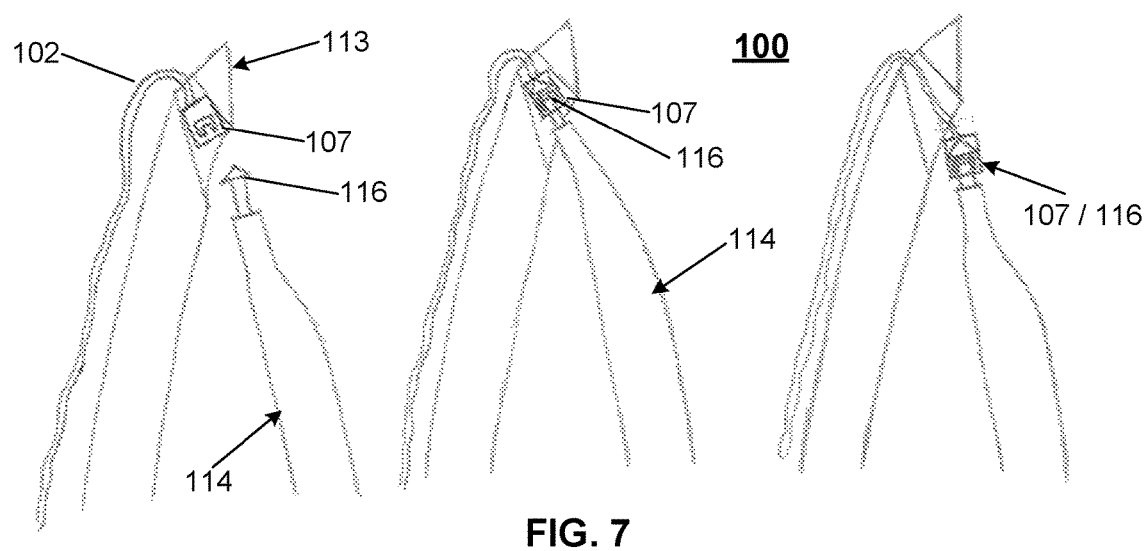
FIG. 7
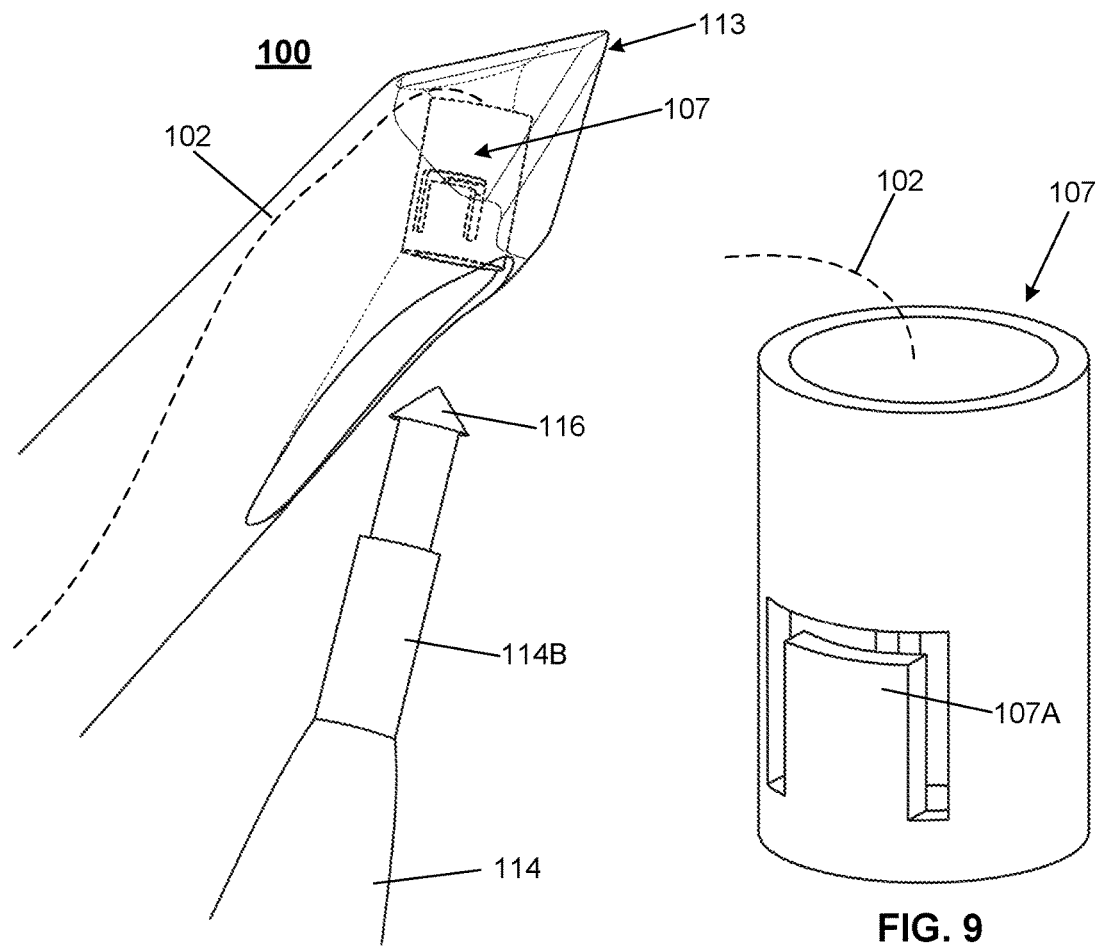
FIG. 8
FIG. 9

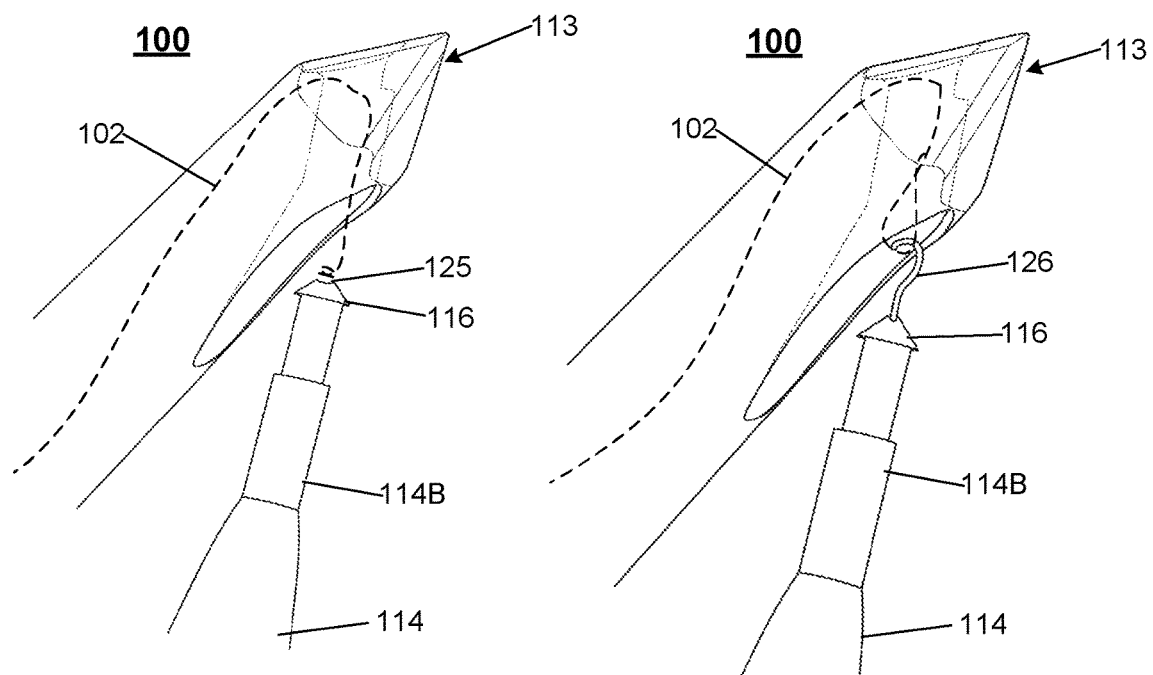
FIG. 10A
FIG. 10B
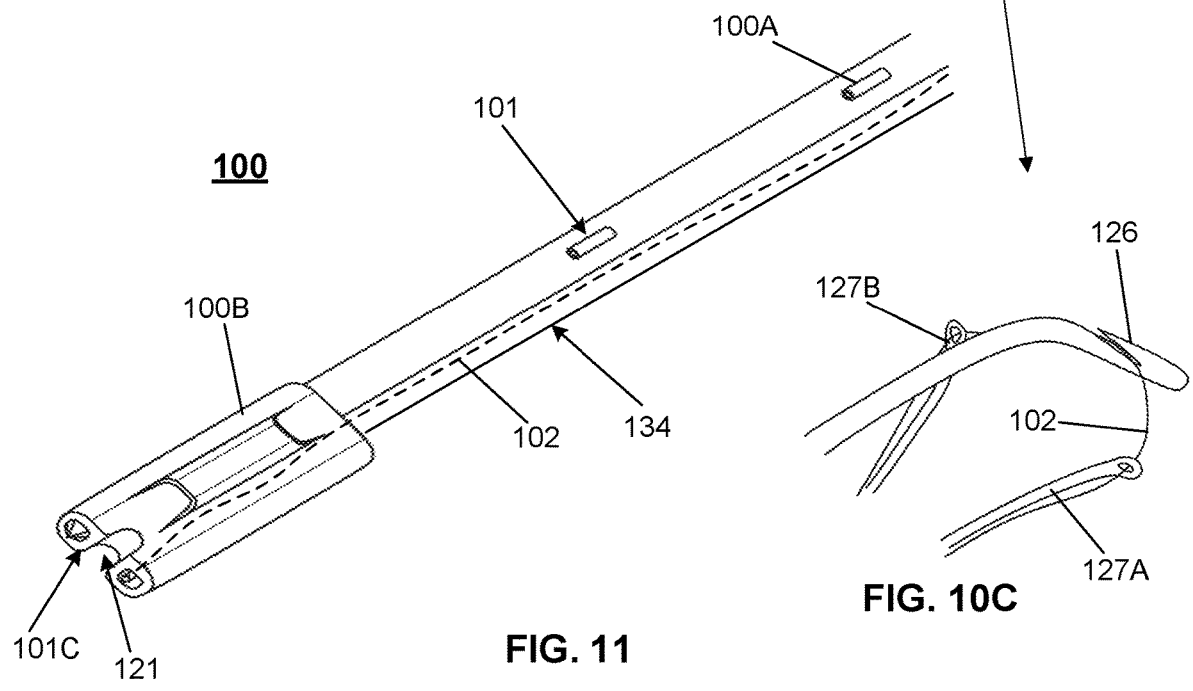
FIG. 11
FIG. 10C

MEDICAL SECURING DEVICE FOR SECURING AN OBJECT WITH A SECURING MEMBER

TECHNICAL FIELD OF THE INVENTION

The invention relates to a medical securing device for securing an object, such as a cardiac implant (for example annuloplasty ring) device with a securing member, such as a suture. In particularly the invention relates to a catheter-operated or cannula-operated medical securing device for securing the cardiac implant device into an annulus of a heart valve, such as a mitral valve or tricuspid valve, comprised of valve tissue and including the annulus and a plurality of leaflets. However, the principle of the invention can also be applied for an open-heart operated medical securing device, as well as securing also other object as only the cardiac implant devices, such as tissue or skin transplant beneath the skin or the like. In addition the invention can also be used for securing an artificial heart valve, for example.

BACKGROUND OF THE INVENTION

FIG. 1A illustrates a portion of the heart 12, the mitral valve 18, and the left ventricle 14. The mitral valve is at its boundary circumferenced by an annulus 20. The valve has two cusps or leaflets 22, 24. Each of these cusps or leaflets 22, 24 are connected to a respective papillary muscle 27, 29 via their respective connecting chordae 26, 28. In normal healthy individuals the free edges of the opposing leaflets will close the valve by coaptation. However, for some individuals the closure is not complete, which results in a regurgitation, also called valvular insufficiency, i.e. back flow of blood to the left atrium making the heart less effective and with potentially severe consequences for the patient. FIG. 1B illustrates a mitral valve 18, in which the leaflets 22, 24 do not close properly. This commonly occurs when the annulus 20 becomes dilated. One surgical procedure to correct this is to remove a portion of the leaflet 24 and stitch the cut edges together with one another. The procedure will pull back the annulus 20 to a more normal position. However the strength of the leaflet 24 is altered. Similar problems with a less effective heart function occur if one or both leaflets are perforated to such an extent that blood is flowing towards the left atrium, although the leaflets close properly.

In some conditions of degenerated heart function, the leaflets do not present a solid surface, as in a degenerative valve disease. The leaflet may also be ruptured, most commonly at an edge of a leaflet, resulting in an incomplete coaptation. Hence, cardiac devices and methods are developed for repairing of one or more leaflets of a heart valve, or other related anatomical structures, such as the chordae attached to the ventricular side of leaflets.

FIGS. 2A and 2B illustrate a prior art cardiac implant device and method for repairing of one or more leaflets of a heart valve as is described in the applicant's previous EP-patent (EP 1 853 199 B1), where the device 40 comprises a first and a second loop-shaped support 42, 44, which are connected to each other by means of a connecting part 48 so as to form a coil-shape. The coil-shape of the device is advantageous during insertion, since the device 40 may then be rotated into position, as described in the patent in more details. One of the supports 44 may be open, e.g. C or D or any other anatomical shaped such that the support 44 presents an end to lead the movement of the support 44 when being rotated into position. The position of the supports 42, 44 are secured by fasteners 56, which are inserted and fastened by hand or small screwdriver.

It is found that the prior art cardiac implant devices, such as depicted above, work very well, but there are still some disadvantages relating to the securing of the cardiac device into the annulus of the heart valve. The cardiac devices are typically manually sutured by a traditional needle and yarns, which is time consuming, because in practise it is needed at least seven knots to be tied in order to have even some certainty that the device is secured. In addition, if the device is sutured by one yarn, which has a drawback namely if one or more knots is/are loosen or the yarn is broken, then the whole securing will come loosen or broken.

In addition with the previous suturing devices it has been difficult to suture in the correct position, thereby providing insufficient suturing strength, and also resulting in a very time consuming procedure, which increases the risks for the patient. Previous suturing devices are also not sufficiently compact for catheter based procedures, for example. There is therefore a need to provide an improved suturing device that solves these issues.

The cardiac implant devices can also be secured by screws. However, the screws are very small, the assembling, positioning and controlling of which are extremely difficult. The screws must be inserted through the both the first and second (upper and lower) loop-shaped support portions 42, 44 (tiny holes in both of the portions), which is highly demanding, because if the first screw is tightened too much, it will distort the portions little bit and thus misaligning the other holes and thereby making it impossible to inserting the other screws. Furthermore there is a huge risk to drop the small screws into the cardiac structure, because for example any safety blankets cannot be used. In addition also magnetic material cannot be used due to possible later magnetic imaging.

SUMMARY OF THE INVENTION

It is an object of the invention to alleviate and eliminate the problems relating to the known prior art. Especially the object of the invention is to provide a medical securing device for securing an object, such as especially a cardiac implant device with a securing member into a tissue, especially into an annulus of a heart valve in an easy, fast, safe and accurate manner with a high degree of control.

The object of the invention can be achieved by the features of independent claim.

The invention relates to a medical securing device for securing an object with a securing member into a tissue, wherein the medical securing device comprises an elongated sheath comprising proximal and distal ends and a securing member introduction device having proximal and distal ends, and said distal end being configured to extend from the sheath. in addition the medical securing device comprises a guiding trail, and at least one point of the securing member introduction device is configured to travel along said first guiding trail and thereby control a defined movement of the distal end of said securing member introduction device when extending from the sheath and so to introduce the portion securing member to the object and to secure said object to the tissue with the securing member.

The medical securing device may be for example a suturing device for suturing the cardiac implant device into the annulus of the heart valve, but also other objects can be secured, such as other implants or portions of a tissue into a second tissue. The implant can be either artificial implants or natural implants. The cardiac implant device may be any cardiac implant device known from prior art, such as described in FIGS. 1-2 and having ring or double ring (helical) shape especially for mitral implant, but also any further application or other device, like a ventrical or atrium or septum correction patch or device or for example a heart valve prosthesis.

According to an embodiment of the invention a medical securing device for securing an object, such as the cardiac implant device, comprises an elongated sheath extending in a longitudinal direction and having proximal and distal ends. The distal end of the elongated sheath comprises a support portion to support the elongated sheath to the object, such as to the cardiac implant device and/or to the tissue. The medical securing device comprises also a securing member introduction device, like a catheter, extending from the sheath and having proximal and distal ends, and having advantageously a needle or tip portion configured to penetrate or puncture into or through the tissue. The distal end of the securing member introduction device is configured to introduce, such as deliver and possibly manipulate, like bend or twist, the securing member, such as a suture, to the object and thereby to secure at least portion of the object to the tissue, such as to the annulus of the valve with the securing member.

In addition the medical securing device, advantageously the elongated sheath, comprises a first guiding trail, such as a groove, which is arranged so that at least one point of the securing member introduction device travels along said first guiding trail. Further the first guiding trail is arranged to control a movement, advantageously a pre-defined movement of the distal end of the securing member introduction device, when extending from the sheath. By the movement the distal end of the securing member introduction device is arranged to introduce the securing member to the object in an appropriate manner and thereby to secure the object to the tissue with the securing member.

According to an embodiment the medical securing device may and advantageously additionally comprise a retrieval device at a distal end thereof. The retrieval device may also be implemented as a catheter having a needle or tip portion configured to penetrate or puncture into or through the tissue. When the retrieval device is extended through the tissue, the retrieval device advantageously captures a portion of the securing member, such as a portion of the suture or end portion of a staple or other securing member portion disclosed elsewhere in this document. After capturing the portion of the securing member, the medical securing device is used for securing the object, such as the cardiac implant device by the securing member (or at least by portion of it) to the tissue, like the annulus of the valve.

In addition the medical securing device, advantageously the elongated sheath, comprises additionally a second guiding trail, such as a groove, which is arranged so that at least one point of the retrieval device travels along said second guiding trail. Further the second guiding trail is arranged to control a movement, advantageously a pre-defined movement of the distal end of the retrieval device, when extending from the sheath. By the movement the distal end of the retrieval device is arranged to capture a portion of the securing member introduced by the securing member introduction device in an appropriate manner and thereby to secure the portion of the securing member to the object, such as to the implant device and/or to the tissue.

According to an advantageous embodiment at least one of said guiding trails is a non-linear guiding trail, whereupon the movement of the distal ends of the securing member introduction device and/or retrieval device can be manipulated by the design of the guiding trails. The guiding trail can have different form, and has advantageously a form of an extended S letter or an integral sign, whereupon the movement track or trajectory of the distal end of the securing member introduction device and/or retrieval device can be pre-defined. According to an embodiment also the form or at least one point of the guiding trail, such as the proximal end of the guiding trail can be adjusted, controlled or otherwise manipulated and thereby the movement track or trajectory of the distal end of the securing member introduction device and/or retrieval device can be changed in an appropriate manner in view of the object, for example, to be secured.

However, at least one of the guiding trail may also be a linear guiding trail, which is arranged so that at least one point of the retrieval device or securing member introduction device travels along said linear guiding trail. In this embodiment at least one portion of the device, such as portion where the distal end of the retrieval device or securing member introduction device extends out from the shield, functions as a support point and thereby forces said at least one point of the retrieval device or securing member introduction device to travel along said linear guiding trail and thereby causing a non-linear and advantageously pre-defined movement of said distal end when extending out from the shield.

By the selection of an appropriate form of the guiding trails the sheath portion and thus also the whole introduction and/or retrieval device or at least the distal end of the device can be made very narrow and small which is clear advantage. In particular this is advantageous namely the medical securing device is typically, at least according to an embodiment, introduced to the object by a catheter. When the device is narrow and small, possible damages caused e.g. to artery or other anatomical structures of the patient in question can be minimized, as well as any medical drawbacks or symptoms are lower than e.g. in the traditional operations. In addition also the patient recovery process is much faster.

The securing member introduction device as well as also the retrieval device can have different types of tip portions, and may comprise either linear or pre-curved needle, for example. For instance, the tip portion may be configured for penetrating and/or puncturing into or through the tissue. Additionally, using of an atraumatic type tip portion is very advantageous namely it does not cut the tissue as such but rather it penetrates between the tissue fibers and displaces them making no cut into the tissue. In addition if the tip portion is pre-curved it also additionally facilitate to manage the trajectory of the distal end of the securing member introduction device and/or retrieval device in a natural way.

However, the form and type of the tip portions can be selected depending on the application, and can be for example a cutting needle, if there is need to puncture the skin and for example securing a tissue or skin transplant beneath the skin.

In addition, depending on the application the securing member may be a suture, staple, helical clip, locking clip, spring clip, or circular clip, and comprising shape memory material, metal or polymer or other suitable material. In embodiments describing the current invention the suture is used as an advantageous example of the securing member. However it should be understood that also other type securing members can be used and these are only examples.

According to an embodiment the medical securing device may comprise also an actuating member coupled with the securing member introduction device and/or retrieval device, so to extend or output from the sheath, for example.

The actuating member may be configured to provide a back-and/or-forth (so out and/or in) movement of the securing member introduction device and/or the retrieval device, when operated. In addition or alternatively the actuating member may be used for adjusting or chancing the form or at least one point of the guiding trail, as discussed elsewhere in this document. Most advantageously the actuating member is managed at the proximal end of the medical securing device and outside a patient to be operated. However, it is to be noted that the actuating member can be located and operated in principle anywhere in connection with the device and that the invention is not limited to only to examples described literally.

In addition the actuating member can be implemented e.g. by push rods, which can be manually operated or automatically or semi-automatically operated. According to an embodiment the actuating members are coupled with the securing member introduction device and retrieval device so that they are managed as cam driven system and change the linear movement of the actuating member to non-linear movement of the securing member introduction device and retrieval device or at least the distal ends thereof.

In addition according to an embodiment the actuating members, in particularly the push rods, can be implemented by catheter operated members being one inside another, or alternatively located next each other in a common catheter or the like.

The medical securing device may comprise also a spring or pre-stringed spring or a pressure accumulator, which can help the operation of the actuating member. For example, according to an embodiment the medical securing device comprises an operation member and the pre-stringed spring or pressure accumulator coupled with the actuating member. When the operator manipulates, such as press, the operation member, it controls the pre-stringed spring or pressure accumulator, which again pushes the securing member introduction device and/or retrieval device outside the sheath. In addition the medical securing device may comprise a second pre-stringed spring or pressure accumulator, which again retracts the securing member introduction device and/or retrieval device inside the sheath after securing operation or in order to finalize the securing operation. It is to be noted that both the securing member introduction device and retrieval device can have own separately operated actuating members. In addition the actuating member can be implemented by a hydraulic or pneumatic arrangement whereupon there is a hydraulic or pneumatic hose, for example, conducting and inducing the pressing and retracting force to the securing member introduction device and/or retrieval device under operation.

When the actuating member are operated automatically or semi-automatically, the operator can focus to more important tasks, such as for addressing and focusing the distal end of the medical securing device to an appropriate position, which is a clear advantage. In addition according to an embodiment the operation of the actuating member may be as a single back-and-forth movement of the securing member introduction device and/or retrieval device, or alternatively the operation may comprise a number of back-and-forth movements.

In addition according to an embodiment an opening angle or distance between the securing member introduction device and retrieval device can be controlled, such as opened or closed, whereupon the amount of the tissue to be received between the devices can be controlled. By this also the settling and locating of the securing member, like the suture, can be accurately controlled. In addition also the trajectory of the distal ends can be controlled by manipulating the opening angle or distance.

The present invention offers advantages over the known prior art, such as an easy, safe, precise and time saving manner to reliable securing the object to the tissue, such as the cardiac implant device into the annulus of the valve with the securing member. In addition, the present invention provides for a compact medical securing device, such as a suturing device, that facilitates suturing and fixation of objects, such as a cardiac implant device, especially an annuloplasty implant, to the tissue. It is to be noted that also portion of the tissue can be secured into other tissue or portion of the tissue, as well as skin transplants can also be secured just beneath the skin Furthermore it is particularly easy to suture beneath a tissue wall, such as the annulus of a heart valve, from the opposite side facing an operator, which otherwise is cumbersome due to the limited visibility or in case of no visibility. The compact medical securing device allows it to be catheter deliverable for a minimally invasive procedure. Furthermore, when using the catheter-operated or cannula-operated medical securing device, risks for having any medical drawbacks or symptoms are much lower than e.g. in the traditional open-heart operation. Also the patient recovery process is much faster. In addition the using of the medical securing device according to the present invention is very clear, logical and straight for the user, namely the securing operation can be done advantageously by one continuous movement.

The exemplary embodiments presented in this text are not to be interpreted to pose limitations to the applicability of the appended claims. The verb "to comprise" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which:

FIGS. 3A-19 illustrate examples of medical securing devices according to advantageous embodiments of the invention.

DETAILED DESCRIPTION

Figure 1A:
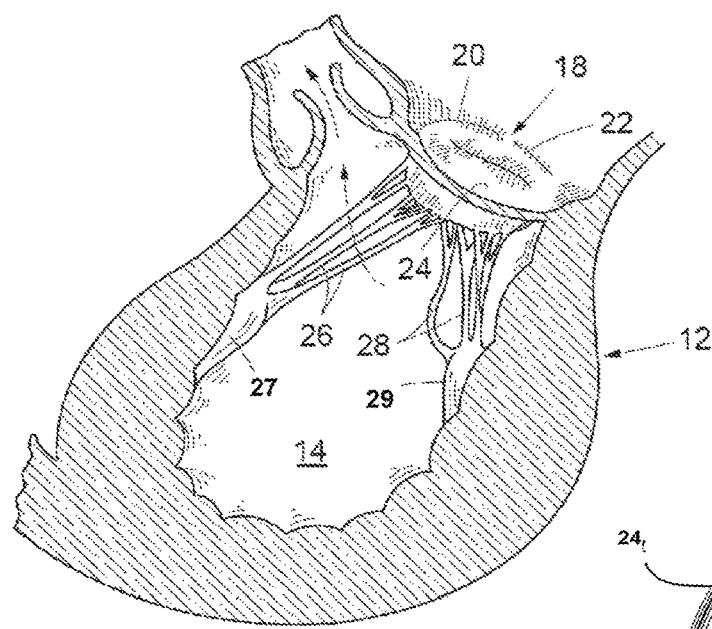
FIGS. 1A-1B illustrate schematically a portion of a heart and mitral valve.
Figure 1B:
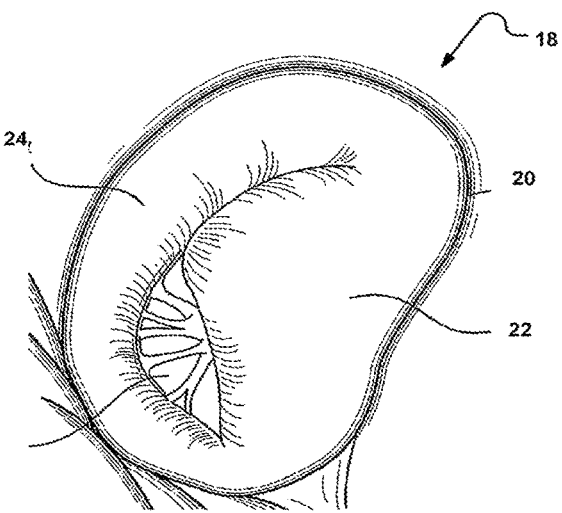
Figure 2A:
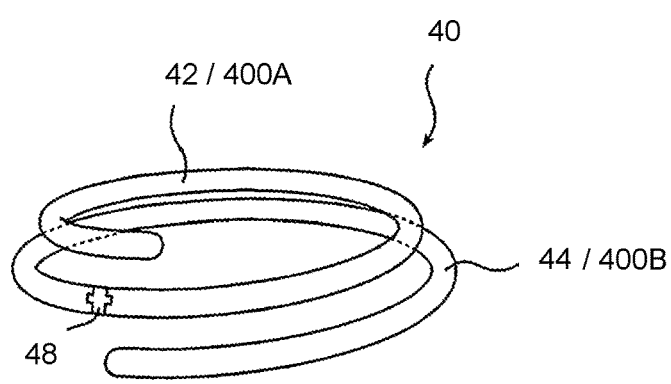
FIGS. 2A-2B illustrate a prior art cardiac implant device for repairing of one or more leaflets of a heart valve.
Figure 2B:
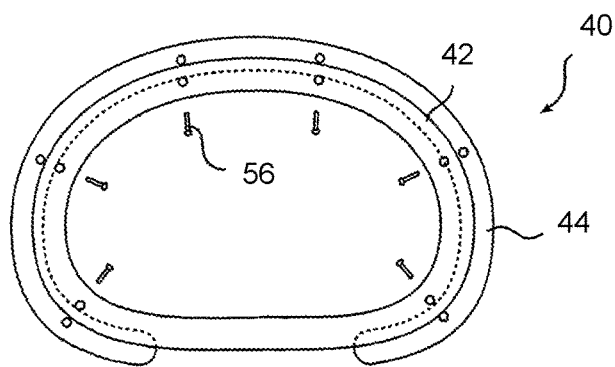
Figure 5A:
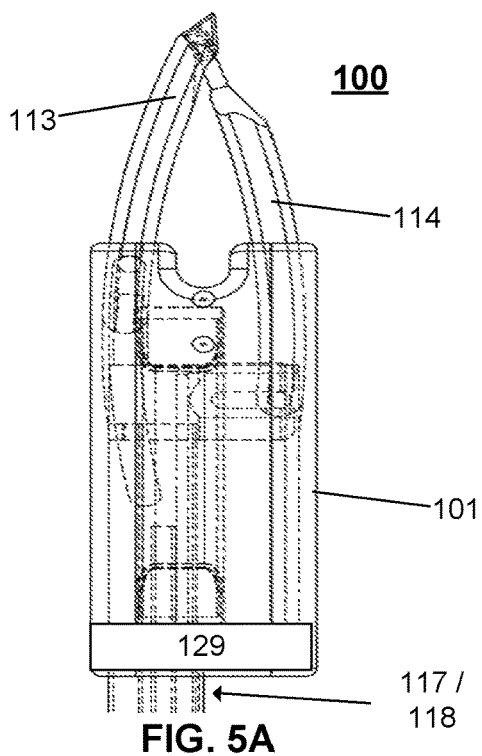
Figure 5B:
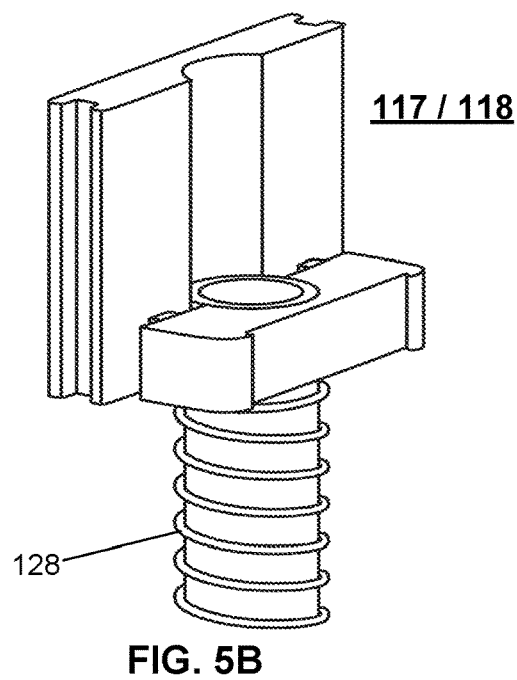

FIGS. 1A-1B and 2A-2B are already discussed in more details in connection with the background of the invention portion above.

FIGS. 3A-19 illustrate examples of medical securing devices 100 for securing an object, especially a cardiac implant device 40, 400A-400B, according to advantageous embodiments of the invention. In particularly a suturing device 100 is described, even if the medical securing device can also be applied with another types of the securing members as discussed elsewhere in this document. The medical securing device 100 comprises an elongated sheath 101 extending in a longitudinal direction and having proximal 101A and distal 101B ends. The distal end of the elongated sheath comprises a support portion 101C to support the elongated sheath to the cardiac implant device directly or to the tissue 20 opposite e.g. the lower portion ring 400B of the cardiac implant device.

The medical securing 100 device comprises also a securing member introduction device 103, 113 having proximal 103A, 113A and distal 103B, 113B ends. The distal end 103B, 113B is configured to extend from the sheath 101, advantageously when operated, and to provide and introduce the securing member 102, such as a suture, to the object and/or to the tissue.

The medical securing device comprises additionally a first guiding trail 105 arranged so that at least one point 103C, 113C of the securing member introduction device 103, 113 travels along said first guiding trail 105, when operated. In this way the medical securing device can control the movement of the distal end 103B, 113B of the securing member introduction device 103, 113 in a defined manner when extending from the sheath 101, and introduce the securing member 102 to the object 400A, 400B and again to secure the object to the tissue 20 with the securing member 102. The movement or trajectory of the distal end 103B, 113B can be pre-defined by selecting the form or shape of the first guiding trail in an appropriate manner.

The medical securing device 100 comprises advantageously also a retrieval device 104, 114 for capturing at least portion of the securing member 102 introduced by the securing member introduction device 103, 113. The retrieval device 104, 114 comprises proximal 104A, 114A and distal 104B, 114B ends, and the distal end 104B, 114B is configured to extend from the sheath 101.

After capturing said portion the device is arranged to secure the portion of the securing member 102 to the object 400A, 400B and/or to the tissue 20. The object is advantageously an implant device 400A, 400B, but can also be for example another portion of the tissue or a portion of another tissue to be secured to the tissue.

The medical securing device comprises advantageously also a second guiding trail 106 arranged so that at least one point 104C, 114C of the retrieval device 104, 114 travels along the second guiding trail 106, when operated. In this way the medical securing device can control the movement of the distal end 104B, 114B of the retrieval device 104, 114 in a defined manner when extending from the sheath 101 and allowing the capture of the portion of the securing member 102.

The first and/or second guiding trails 105, 106 are advantageously implemented by grooves or slots or the like, which are configured to control the movement of the distal ends 103B, 113B, 104B, 114B of the securing member introduction device 103, 113 and retrieval device 104, 114 during the operation and moving of the securing member introduction device 103, 113 and retrieval device 104, 114. The first and/or second guiding trails 105, 106 are advantageously arranged into the distal end 101B or the medical securing device or the sheath 101, as can be seen especially in FIGS. 3A-3C and 4A-4D.

According to an advantageous embodiment the guiding trails 105, 106 are non-linear guiding trails, as can be seen e.g. in FIGS. 3A-3C. The guiding trails 105, 106 can be implemented, depending on the design of the medical securing device, in different ways. The form of the guiding trails 105, 106 can be for example an extended S letter or an integral sign, as is the case in FIGS. 3A-3C. and where the first and second guiding trails 105, 106 cross each other and extend from the first side of the elongated sheath 101 to the second opposite side of the elongated sheath 101 (so from left to right and other from right to left, vice versa).

An alternative implementation is illustrated in FIGS. 4A-4D, where the first guiding trail 105 has a curvature form or shape and the second guiding trail 106 is a linear or straightforward groove or slot. Anyway, in all cases the guiding trails 105, 106 are arranged so that when extending the distal ends 103B, 113B, 104B, 114B from the sheath 101, said defined movement of the distal ends 103B, 113B, 104B, 114B is achieved and that the movement is in addition a non-linear movement. This allows to manufacture a very narrow and small sheath portion or device. In addition to guiding trails there might also be additional guiding members for guiding especially the movements of the distal ends 103B, 113B, 104B, 114B, such as a spring 119A in FIGS. 3A-3C or a structural arrangement like a tapered canal portion 119B in FIGS. 4A-4D through which the body or arm of the securing member introduction and retrieval devices 113, 114 must travel.

The retrieval device 104, 114 comprises also a facing element 115, 116 at the distal end 104B, 114B of it for facing or receiving the distal end 103B, 113B of the securing member introduction device 103, 113 and thereby for guiding said distal ends 103B, 113B, 104B, 114B to meet each other. During facing the portion of the securing member 102 is introduced to the distal end 104B, 114B of the retrieval device 104, 114B, thereby allowing the retrieval device 104, 114 to capture the portion of the securing member 102 and to secure the portion of the securing member 102 to the object 400A, 400B and/or to the tissue 20. The facing element 115, 116 at the distal end 104B, 114B may be e.g. a hole or through hole or a slit or gap 115. Also other types of facing elements can be applied, such as tip portion 116 with thick or expansion circumference area. In addition it is to be noted that the facing element 115, 116 can be provided with an additional element for guiding and facilitating the receiving of the securing member, such as with a suction or under pressure providing element 125 (see FIG. 10A) or with a hook-shaped portion 126 (see FIG. 10B) so to engage and capture at least a portion of said securing member 102, such as advantageously the suture.

The securing member introduction device 103, 113 and/or the retrieval device 104, 114 may be operated by using an operation arm 124, which is advantageously in the proximal end 101A of the medical securing device 100 or the sheath 101. The operation arm 124 is advantageously coupled with an actuating members 117, 118, and configured to cause during an operation of it back-and-forth movements 110 of the actuating members and thereby a back-and-forth movements (out-in movements in relation to the sheath) of the securing member introduction device 103, 113 and/or the retrieval device 104, 114, correspondingly.

Depending on the embodiment an order of the securing member introduction device 103, 113 and/or the retrieval device 104, 114 can vary. For example in relation to the medical securing device 100 illustrated in FIGS. 3A-3C, the retrieval device 104 is configured to be extended from the sheath 101 before the securing member introduction device 103. In more details, during the operation, the retrieval device 104 is configured to move at first out from the sheath 101 so that the distal end 104B of it makes advantageously a non-linear movement so that it is able to curve into the "back side" of the object 400A, 400B, as can be seen in FIG. 3B. Right after this the securing member introduction device 103 is configured to move out from the sheath 101 so that the distal end 103B of it makes advantageously a non-linear movement so that it is also able to curve into the "back side" of the object 400A, 400B, as can be seen in FIG. 3C, and additionally to meet the facing element 115 of the retrieval device 104.

In this particular embodiment (FIGS. 3A-3C) the facing element 115 of the retrieval device 104 comprises a hole or a slot 115 through which the distal end 103B of the securing member introduction device 103 moves in a back-and-forth manner. According to an example the securing member introduction device 103 moves at first into or through the facing element 115 and introduces the portion of the securing member 102 to the facing element 115, such as for example a knot or other expansion portion of the suture to the edge portion of the hole or slit type facing element 115. The retrieval device may move little bit back, thereby capturing the portion of the securing member 102, such as the knot or expansion portion of the suture to the edge portion of the hole or slit. After this the securing member introduction device 103 moves back and away from the hole or slit type facing element 115.

Next, depending on the application, either the securing member introduction device 103 and the retrieval device 104 with the portion of the securing member 102 may both move essentially at the same time back to the sheath 101, or alternative the securing member introduction device 103 may move as first and the retrieval device 104 as a second. If the both are moving back in the same time, a forming of a possible loop of a suture 102 can be avoided, which can otherwise even cause damages to the tissue or making damages to the suture itself, if e.g. the securing member introduction device 103 is moved back first, and letting thereby the suture make an additional loop (between the distal ends 103B, 104B), before the retracting of the retrieval device 104.

When retracting the securing member introduction and retrieval devices 103, 104, the portion of the securing member 102 is advantageously secured to the object 400A, 400B and/or to the tissue 20.

Another example is illustrated in FIGS. 4A-4D, where the securing member introduction device 113 is configured to be extended from the sheath 101 before the retrieval device 114. In more details, during the operation, the securing member introduction device 113 is configured to move at first out from the sheath 101 so that the distal end 113B of it makes advantageously a non-linear movement so that it is able to curve into the "back side" of the object, as can be seen in FIG. 4B. Right after this the retrieval device 114 is configured to move out from the sheath 101 so that the distal end 114B of it makes advantageously a non-linear movement so that it is also able to curve into the "back side" of the object 400A, 400B, as can be seen in FIG. 4C, and additionally to allow the facing element 116 of the retrieval device 114 to meet the distal end 113B portion of the securing member introduction device 113.

When meeting the distal end 113B portion of the securing member introduction device 113, the retrieval device is configured to capture the portion of the securing member 102, such as the suture, as is illustrated in FIG. 4D. When retracting the securing member introduction and retrieval devices 113, 114, the portion of the securing member 102 is advantageously secured to the object 400A, 400B and/or to the tissue 20.

It is to be noted that the securing member introduction device 113 and the retrieval device 114 may both move essentially at the same time back to the sheath 101, or alternative the retrieval device 114 may move as first and the securing member introduction device 103 as a second. If the both are moving back in the same time, a forming of a possible loop of a suture can also be avoided, as is the case with embodiment illustrated in FIGS. 3A-3C.

In this particular embodiment (FIGS. 4A-4D) the facing element 116 of the retrieval device 114 may comprise different implementations, as described elsewhere in this document, especially in FIGS. 7, 8, 9 and 10A-10B. The facing element 116 may comprises e.g. the extension portion, and the distal end 113B of the securing member introduction device 113 a counterpart portion 107, such as a snap locking member with a tongue 107A to catch the extension portion 116, or a magnet, to which said portion of said securing member 102 is caught and attached. In this case the counterpart portion 107 with the portion of the securing member 102 is advantageously captured by the facing element 116, like the extended tip portion of the retrieval device 114 thereby allowing the retrieval device 114 to capture the portion of the securing member 102. As an example the capturing is performed during in a single back-and-forth movement of the retrieval device 104, but it is to be noted, that depending on the implementation, also number of successive back-and-forth movements can be performed.

In addition or alternatively the facing element 116 of the retrieval device 114 may comprise a suction or under pressure providing element 125 (as described in FIG. 10A), whereupon when facing with the distal end 113B securing member introduction device 113, the facing element 116 may capture the portion of the securing member, such as the suture, by the suction or under pressure. Still in addition the facing element 116 of the retrieval device 114 may comprise a hook-shaped portion 126 so to engage and capture at least a portion of said securing member 102, such as the suture, as described in FIG. 10B.

An additional example of the hook-shaped portion 126 is illustrated in FIG. 10O, where the securing member introduction device 113 (advantageously at its distal end) comprises radially displaceable arms 127A, 127B holding the suture 102. The radially displaceable arms 127A, 127B can be pushed out from the securing member introduction device 113 (e.g. a catheter type), thus resiliently biased to diverge and to form an extended shape and to introduce the suture so to form a looped form, or a protrusion portion with a portion of the suture 102, as can be seen in FIG. 10O. The hook-shaped portion 126 can thereby engage and capture the portion of said looped shape suture 102.

It is to be noted that the facing element 116 with the suction or under pressure providing element 125 or with the hook-shaped portion 126 may also be actuated without any counterpart portion 107.

According to an embodiment the actuating member 117, 118 may comprise or at least be coupled with a spring and/or pre-stringed spring 128, pressure accumulator 129 or hydraulic or pneumatic arrangement 130 for facilitating or providing at least one direction of the movement of said back-and-forth movement of the securing member introduction device 103, 113 and/or retrieval device 104, 114. For example, a first pre-stringed spring 128 or pressure accumulator 129 may trigger the out-movement of the securing member introduction device and/or retrieval device, whereupon the back-movement (in) is triggered by the spring or pre-stringed spring 128. Naturally, also other combination can be applied and the force transmission to the actuating member 117, 118 or the securing member introduction and/or retrieval devices can be applied via hydraulic arrangement 130 including also hydraulic hose 131.

Figure 6A:
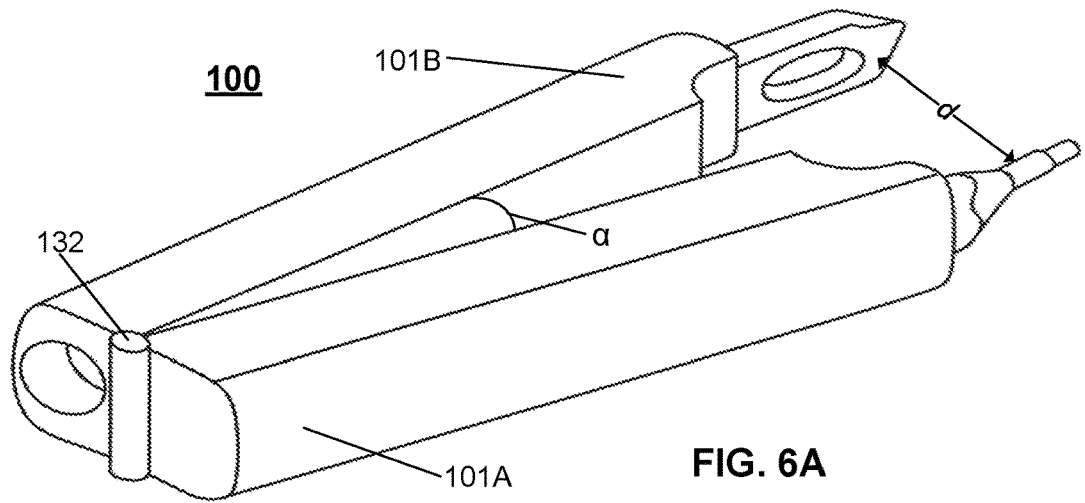
Figure 6B:
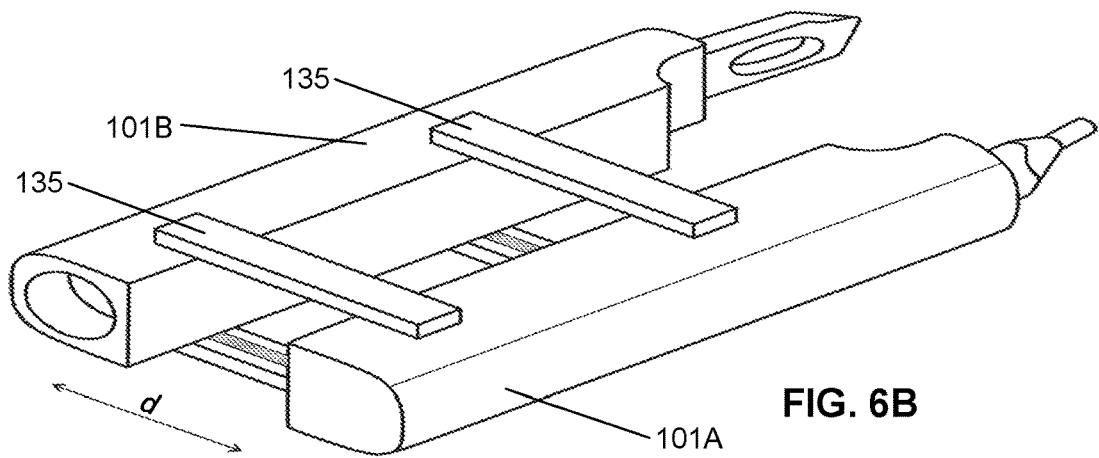

FIGS. 6A and 6B illustrate examples of the medical securing device 100 and especially of the sheath portion 101, where the opening angle α or distance d between the securing member introduction device 113 and retrieval device 114 can be controlled via an hinge 132 or a rail 135, such as opening or closing the angle or the distance. Advantageously the controlling of the opening angle α or distance d can be operated by the operation arm 124. In addition, as can be seen in FIG. 6B, also the distance d between the securing member introduction device 113 and retrieval device 114 can be controlled so that the distance d of both the distal and proximal ends of the sheath 101 can be changed. These allow to control the amount of the tissue to be received between the devices, and thus also the settling and locating of the securing member, like the suture, can be accurately controlled. In addition also the trajectory of the distal ends 103B, 113B, 104B, 114B can be controlled by manipulating the opening angle α or distance d.

In addition it is to be noted that according to an embodiment also the form or at least one point of the guiding trail 105, 106, such as the proximal end 105A 106A of the guiding trail can be adjusted 133, controlled or otherwise manipulated and thereby the movement track or trajectory of the distal end of the securing member introduction device and/or retrieval device can be changed in an appropriate manner in view of the object. The medical securing device 100 comprises advantageously an adjusting device 134 for adjusting 133 the form or shape or other parameters of the guiding trail.

Figure 13:
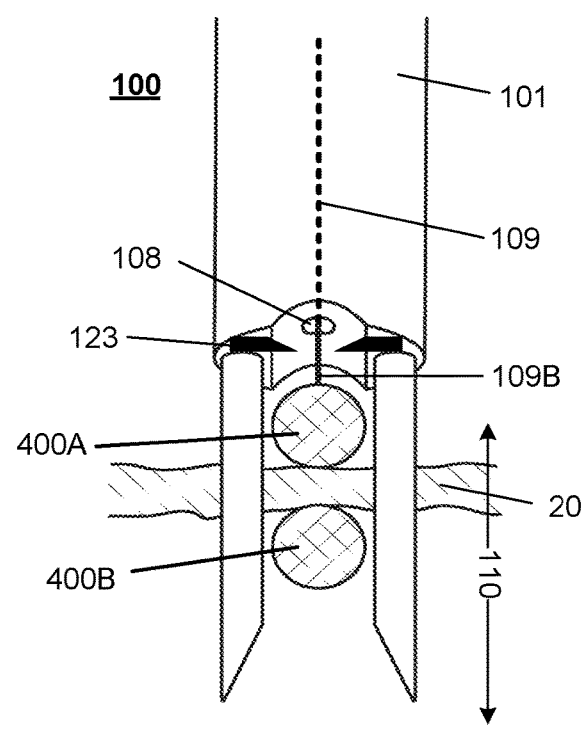
Figure 14:
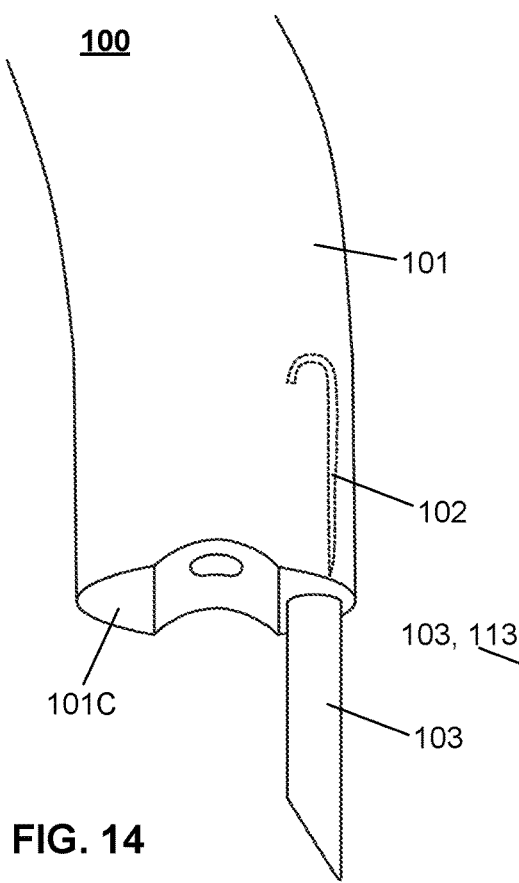
Figure 16:
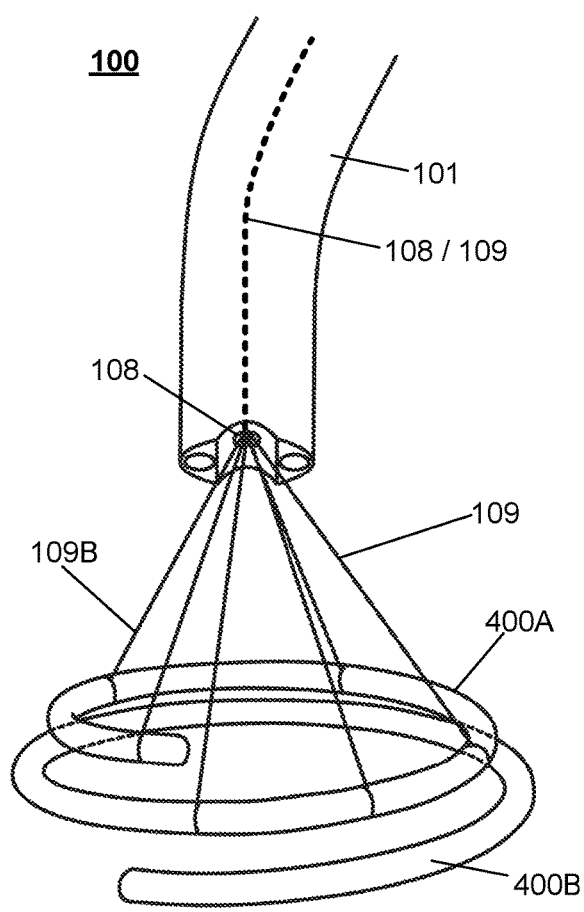

In addition the medical securing device 100, in particularly the sheath 101 may also comprise a conduit 108 between the proximal and distal ends 100A, 100B (101A, 101B) for receiving at least one guiding wire 109 coupled with the object to be secured (optional feature), as is described in FIGS. 13 and 16. If the object to be secured is provided with the guiding wire 109, the distal end 109B of is advantageously fixed to the object 400A, 400B so to guide the device along said guiding wire and to support a support portion 101C or a special recess 121 of the distal end 101B of the elongated sheath 101 to the object 400A, 400B to be secured.

In addition the medical securing device 100 may also comprise a cutting member 123 for cutting the guiding wire 109 in the vicinity of the object 400A, 400B or the tissue 20. The device 100 may also comprise a cutting member 123 for cutting the suture (as the securing member) by which the object is secured.

Figure 12:
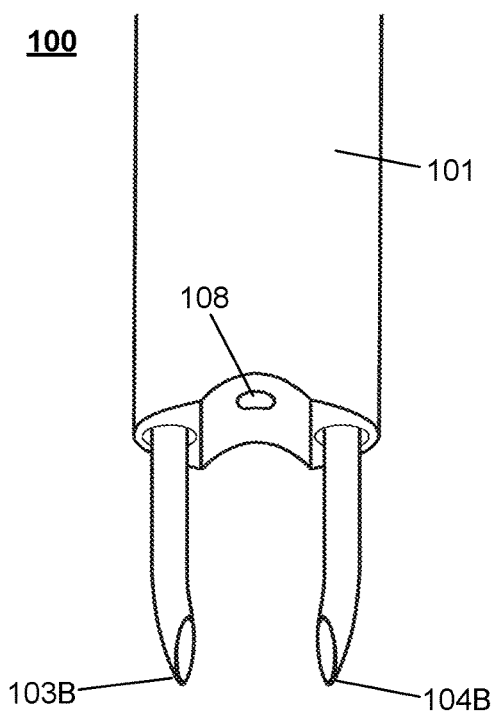

Moreover medical securing device 100, in particularly the sheath 101 may also comprise a conduit 108 between the proximal and distal ends thereof for introducing under pressure into the distal end 101B or to a support portion 101C, 121 of the elongated sheath 101 as is described in FIG. 12. The under pressure is provided in order to suck and thereby to support the elongated sheath 101 or the support portion 101C, 121 to the object 400A, 400B or to the tissue 20 via the force induced by the under pressure and/or for applying counterforce for the introduction movement 110 of the securing member 102.

Figure 15:
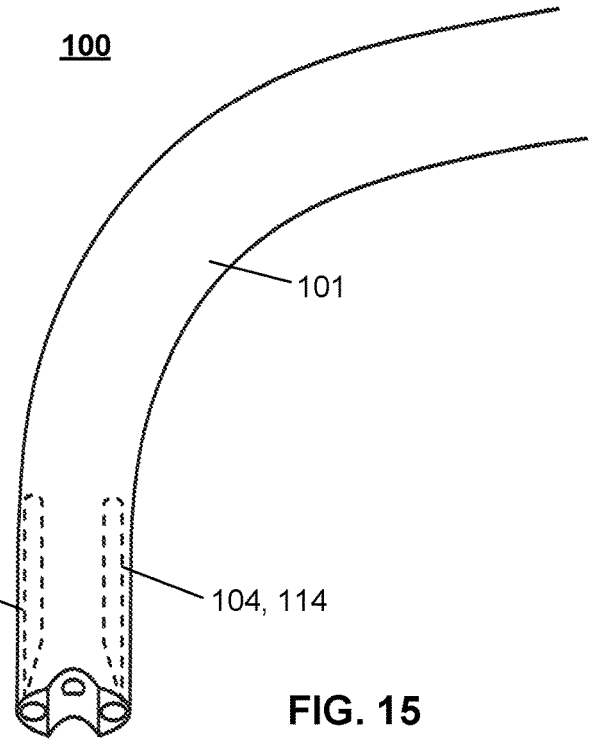
Figure 17:
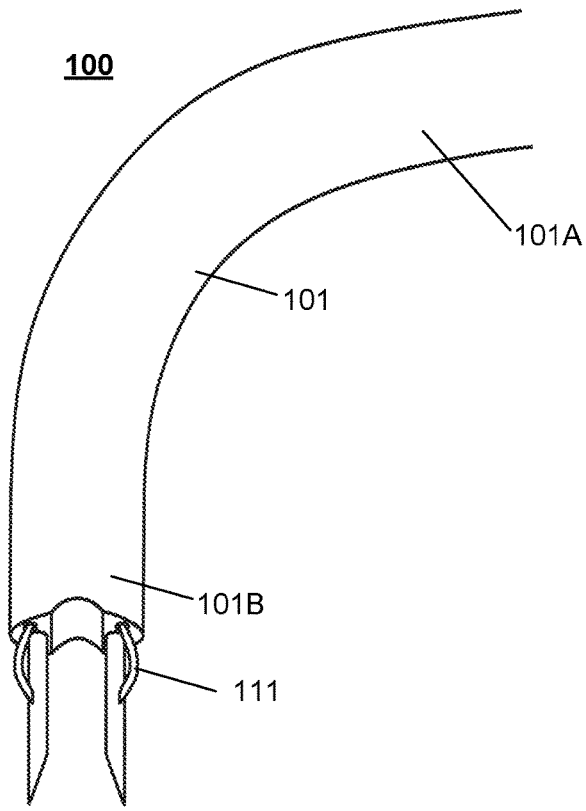

The medical securing device 100 or more precisely the distal end 101B of the elongated sheath 101 may also comprise a locking member 111, which is advantageously configured to lock the distal end 101B of the elongated sheath 101 to the object 400A, 400B or to the tissue 20, as can be seen in FIG. 17. The locking member 111 can be implemented e.g. by a finger or spring, and it might be made of or comprise shape memory material. It may be operable also from the proximal end of the elongated sheath so via operation arm 124, for example. In addition, as can be seen in FIGS. 15 and 17, the elongated sheath can be bendable (like a bendable and controllable catheter), whereupon it can be more easily directed into a right position, as well as that the securing member introduction device 103, 113 and retrieval device 104, 114 can be retracted into the sheath 101 so that no tip portion is located outside the sheath 101, thereby avoiding or at least minimizing any damage to the artery or other anatomical structures of the patient in question during inserting the distal end of the medical securing device 100.

FIG. 11 illustrates an example of the medical securing device 100 with the proximal and distal ends 100A, 100B. It is to be noted that the medical securing device 100 may comprise a catheter type shield 134 structure in connection with the elongated sheath 101, for example to provide the secure members, such as the suture, so that it is covered during the operation.

Figure 18:
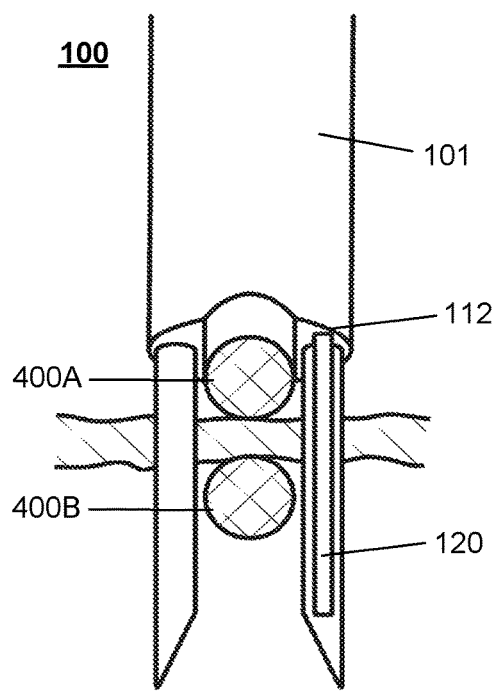
Figure 19:
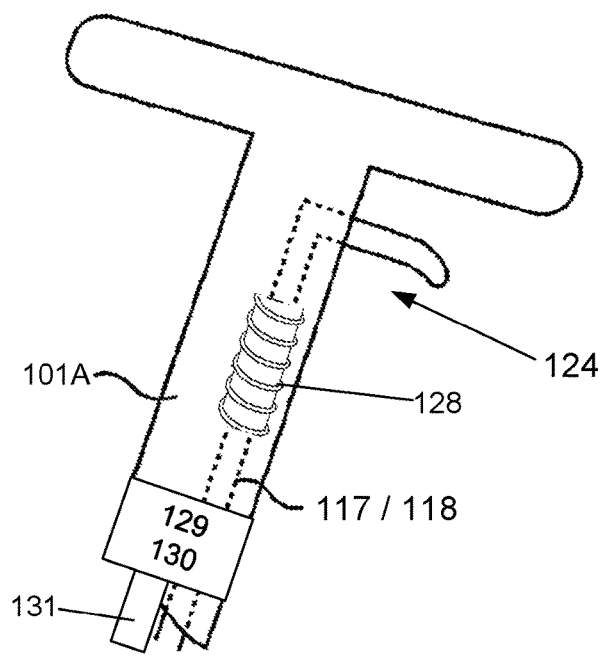

In addition, according to an embodiment the distal end 101B of the elongated sheath 101 may also comprises a guiding trail 112, such as a groove or slot or the like, as is described in FIG. 18. Respectively the tip portion of the securing member introduction device 103, 113 and/or the retrieval device 104, 114 may also comprise a projection 120 as a counterpart for the guiding trail (or vice versa). The guiding trail 112 and projection 120 thereby guide the tip portion of the securing member introduction device and/or the retrieval device so to pierce the tissue 20 without substantive twisting around the longitudinal axis of the tip portion of the device. By this it can be ensured that the position or angle of the distal portions 103B, 113B, 104B, 114B of the securing member introduction device 103, 113 and/or the retrieval device 104, 114 is in a right or suitable position in relation to the object 400A, 400B, for example.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. For example the object to be secured may be e.g. the cardiac implant (for example annuloplasty ring) device, but also other type of object can be secured, as is demonstrated and described in the description, In addition different kinds of securing members can be used, even if the suture is mentioned in the connection with most applications. In particularly it is to be understood that the invention can be applied as a catheter-operated or cannula-operated medical securing device and for securing the cardiac implant device into an annulus of a heart valve, such as a mitral valve or tricuspid valve, comprised of valve tissue and including the annulus and a plurality of leaflets. However, the principle of the invention can also be applied for an open-heart operated medical securing device, as well as securing also other object as only the cardiac implant devices, such as tissue or skin transplant beneath the skin or the like. In addition the invention can also be used for securing an artificial heart valve, for example.

Further, even if the facing elements 115, 116 are described to be located in connection with the retrieval device 104, 114, it should be understood that the facing elements 115, 116 can also be provided into the distal end 103B, 113B of the securing member introduction device 103, 113, correspondingly.

The features recited in dependent claims are mutually freely combinable unless otherwise explicitly stated.

The invention claimed is:

1. A medical securing device for securing an object with a securing member into a tissue comprising:
   an elongated sheath comprising proximal and distal ends,
   a securing member introduction device having proximal and distal ends, and the distal end of the securing member introduction device being configured to extend from the elongated sheath,
   a retrieval device having proximal and distal ends, and the distal end of the retrieval device being configured to extend from the elongated sheath,
   first and second guiding rails that cross each other, wherein the first guiding rail is arranged to extend from a first side of the elongated sheath to a second opposite side of the elongated sheath and only a portion of the securing member introduction device is configured to travel along the first guiding rail and thereby control a defined movement of the distal end of the securing member introduction device, wherein the distal end of the securing member introduction device comprises a tip portion which comprises a pre-curved needle, wherein the distal end of the securing member introduction device is configured to travel outside of the first guiding rail, wherein the distal end of the securing member introduction device is configured to exhibit a non-linear movement when extending from the elongated sheath, wherein the securing member introduction device is configured to introduce a portion of the securing member to the object and to secure the object to the tissue with the securing member, and
   the second guiding rail is arranged to extend from the second side of the elongated sheath to the first side of the elongated sheath and at least one point of the retrieval device is configured to travel along the second guiding rail and thereby control a defined movement of the distal end of the retrieval device so that the distal end of the retrieval device is configured to exhibit a non-linear movement when extending from the elongated sheath and so to capture the portion of the securing member introduced by the securing member introduction device, and to secure the portion of the securing member to the object or to the tissue.

2. The medical securing device of claim 1, wherein the first and second guiding rails are non-linear guiding rails or wherein the guiding rails have a form of an extended S letter or an integral sign.

3. The medical securing device of claim 1, wherein the retrieval device comprises a facing element at the distal end thereof for facing the distal end of the securing member introduction device and to introduce the portion of the securing member to the distal end of the retrieval device, and thereby allowing the retrieval device to capture the portion of the securing member and to secure the portion of the securing member to the object or to the tissue.

4. The medical securing device of claim 1, wherein the retrieval device is configured to be extended from the elongated sheath before the securing member introduction device, and wherein a facing element of the retrieval device is a hole or slit, through which the distal end of the securing member introduction device is configured to move and introduce the portion of the securing member to the hole or slit, and thereby allowing the retrieval device to capture the portion of the securing member and to secure the portion of the securing member to the object or to the tissue after the securing member introduction device is moved away from the facing element.

5. The medical securing device of claim 1, wherein the securing member is a suture.

6. The medical securing device of claim 1, wherein the medical securing device comprises an actuating member for projecting the securing member introduction device or retrieval device from the elongated sheath, and wherein the actuating member is configured to provide a back-and-forth movement of the securing member introduction device or the retrieval device, when operated.

7. The medical securing device of claim 6, wherein the actuating member comprises a spring, pre-stringed spring, pressure accumulator, or hydraulic or pneumatic arrangement, or wherein the actuating member comprises a push rod for providing at least one movement of the back-and-forth movement of the securing member introduction device or retrieval device.

8. The medical securing device of claim 1, wherein the elongated sheath comprises a conduit between the proximal and distal ends thereof for receiving at least one guiding wire, a distal end of the guiding wire being fixed to the object and thereby for guiding a support portion of the distal end of the elongated sheath along said guiding wire and to support the support portion to the object.

9. The medical securing device of claim 8, wherein the distal end of the elongated sheath comprises a cutting member for cutting the guiding wire in the vicinity of the object or the tissue.

10. The medical securing device of claim 1, wherein the elongated sheath comprises a conduit between the proximal and distal ends thereof for introducing pressure into the distal end or to a support portion of the elongated sheath in order to suck and thereby to support the elongated sheath or the support portion to the object or to the tissue via a force induced by the pressure or for applying a counterforce for an introduction movement of the securing member.

* * * * *